United States Patent
Otto et al.

(10) Patent No.: US 7,311,010 B2
(45) Date of Patent: Dec. 25, 2007

(54) GAUGE RESTRAINT MEASUREMENT SYSTEM

(76) Inventors: Daniel P. Otto, 3008 Enterprise Pk. Ave. S., Chicago Heights, IL (US) 60411; Harold Thomas Ruggles, 3819 W. 90th Ct., Merrillville, IN (US) 46410; Martin Conneally, 1000 Holland Dr., Crete, IL (US) 60417

( * ) Notice: Subject to any disclaimer, the term of this patent is extended or adjusted under 35 U.S.C. 154(b) by 212 days.

(21) Appl. No.: 11/207,629

(22) Filed: Aug. 18, 2005

(65) Prior Publication Data

US 2006/0000290 A1   Jan. 5, 2006

Related U.S. Application Data

(62) Division of application No. 10/749,716, filed on Dec. 31, 2003, now Pat. No. 7,007,561.

(60) Provisional application No. 60/437,467, filed on Dec. 31, 2002.

(51) Int. Cl.
    *G01D 1/16* (2006.01)
(52) U.S. Cl. .................................................. 73/798
(58) Field of Classification Search .................. 73/798
    See application file for complete search history.

(56) References Cited

U.S. PATENT DOCUMENTS

| | | |
|---|---|---|
| 2,718,197 A | 9/1955 | Bock et al. |
| 3,020,858 A | 2/1962 | Perkins et al. |
| 3,249,067 A | 5/1966 | Keller |
| 3,263,628 A | 8/1966 | Grove et al. |
| 3,503,339 A | 3/1970 | Kershaw |
| 3,581,671 A | 6/1971 | Hart |
| 3,718,040 A * | 2/1973 | Freeman et al. ............ 73/146 |
| 3,804,925 A | 4/1974 | Elliott |
| 3,869,907 A | 3/1975 | Plasser |
| 3,896,665 A | 7/1975 | Goel |
| 3,980,025 A | 9/1976 | Olson, Sr. et al. |
| 4,044,594 A | 8/1977 | Owens et al. |
| 4,468,966 A | 9/1984 | Bradshaw |
| 4,480,480 A | 11/1984 | Scott et al. |
| 4,534,297 A | 8/1985 | Johnson, Sr. |
| 4,646,749 A * | 3/1987 | Berger et al. ............... 600/491 |
| 4,662,224 A | 5/1987 | Turbe |
| 4,691,565 A | 9/1987 | Theurer |
| 4,708,066 A | 11/1987 | Heckman |
| 4,756,782 A | 7/1988 | Sieberling |
| 5,186,109 A | 2/1993 | Madison |
| 5,339,692 A | 8/1994 | Shoenhair et al. |

(Continued)

OTHER PUBLICATIONS

The Next Generation of Gage Restraint Measurement Systems, Proceedings of IMECI '03 2003 ASME International Mechanical Engineering Congress, Washington, D.C. Nov. 15-21, 2003.

(Continued)

*Primary Examiner*—Max Noori
(74) *Attorney, Agent, or Firm*—Barnes & Thornburg LLP

(57) ABSTRACT

A direct measuring loaded gage axle assembly that measures track strength by directly measuring constant load on split axles as vertical loads are imposed by a hydraulic ram, and horizontal loads being supplied by horizontal rams through split axles and steel wheels to the railroad tracks enabling improved calibration to measure changes in track gauge indicating track strength condition and further including electronic data recording and comparison.

12 Claims, 6 Drawing Sheets

U.S. PATENT DOCUMENTS

| | | |
|---|---|---|
| 5,386,727 A | 2/1995 | Searle |
| 5,522,265 A | 6/1996 | Jaeggi |
| 5,531,122 A * | 7/1996 | Chatham et al. ............... 73/760 |
| 5,617,639 A | 4/1997 | Perry |
| 5,627,508 A | 5/1997 | Cooper et al. |
| 5,756,903 A | 5/1998 | Norby et al. |
| 6,600,999 B2 * | 7/2003 | Clark et al. .................... 702/35 |
| 6,675,077 B2 * | 1/2004 | Dembosky et al. ........... 701/19 |
| 6,681,160 B2 | 1/2004 | Bidaud |
| 6,725,782 B1 | 4/2004 | Bloom et al. |
| 6,983,658 B2 * | 1/2006 | Wenski ........................ 73/800 |

OTHER PUBLICATIONS

Gage Restraint Measurement System, Ensco, Inc. undated.

Judge, AAR's Track Loading Vehicle Still Improving After 5 Years, Jun. 1995.

Ensco, Inc., Instrumented Wheelset Systems, Undated.

Tru-Test Track Loading Vehicle Sales Brochure, 1 Year Before Priority Date.

Kalay, Measuring Lateral and Longitudinal Track Strength, Railway Track and Structures, May 1994.

* cited by examiner

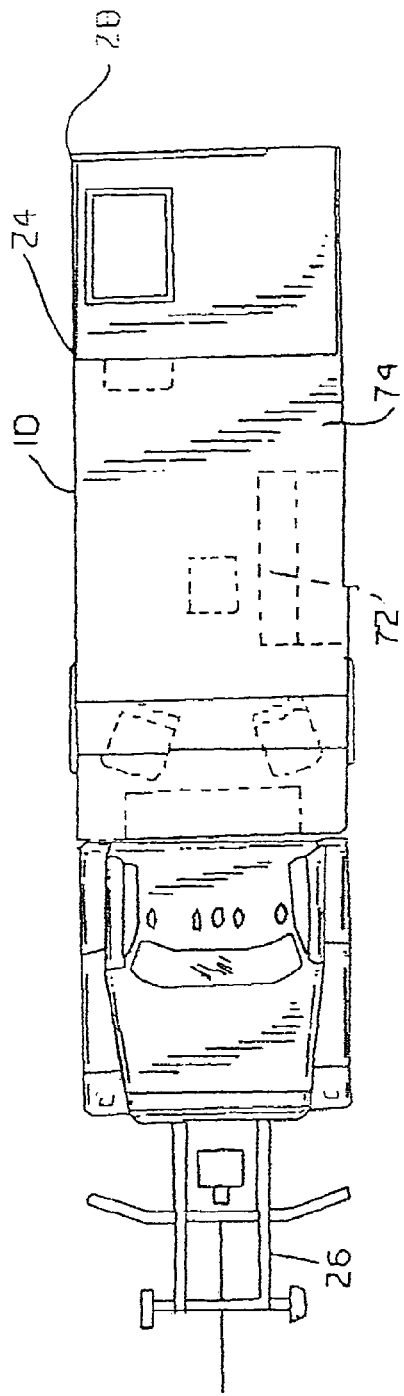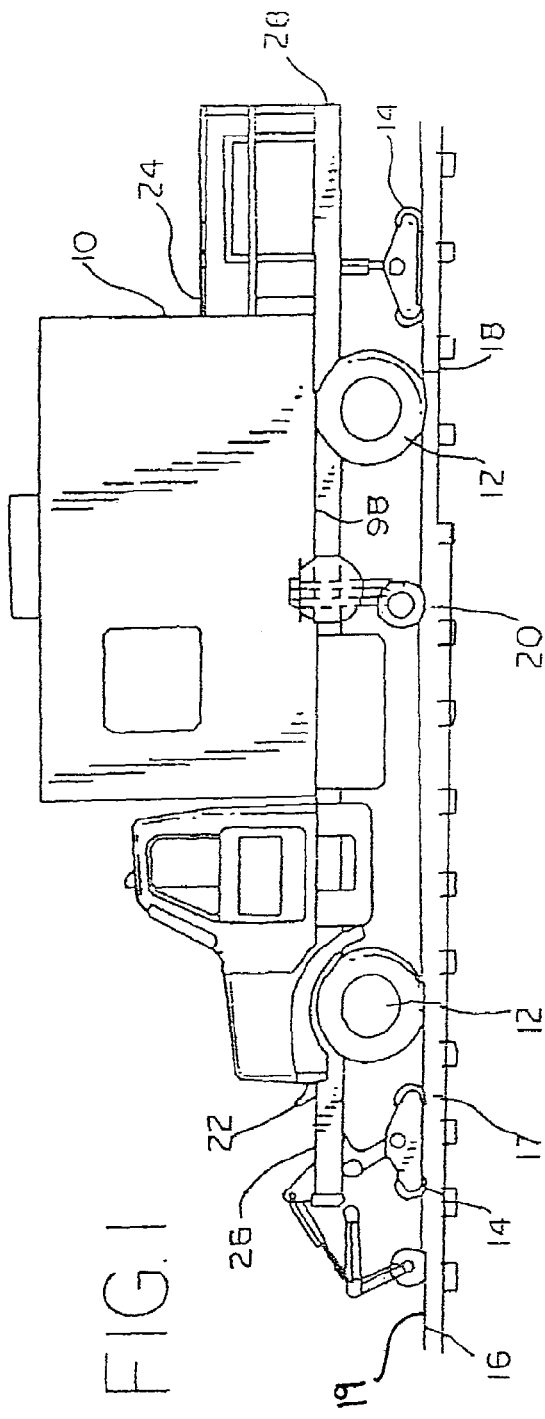

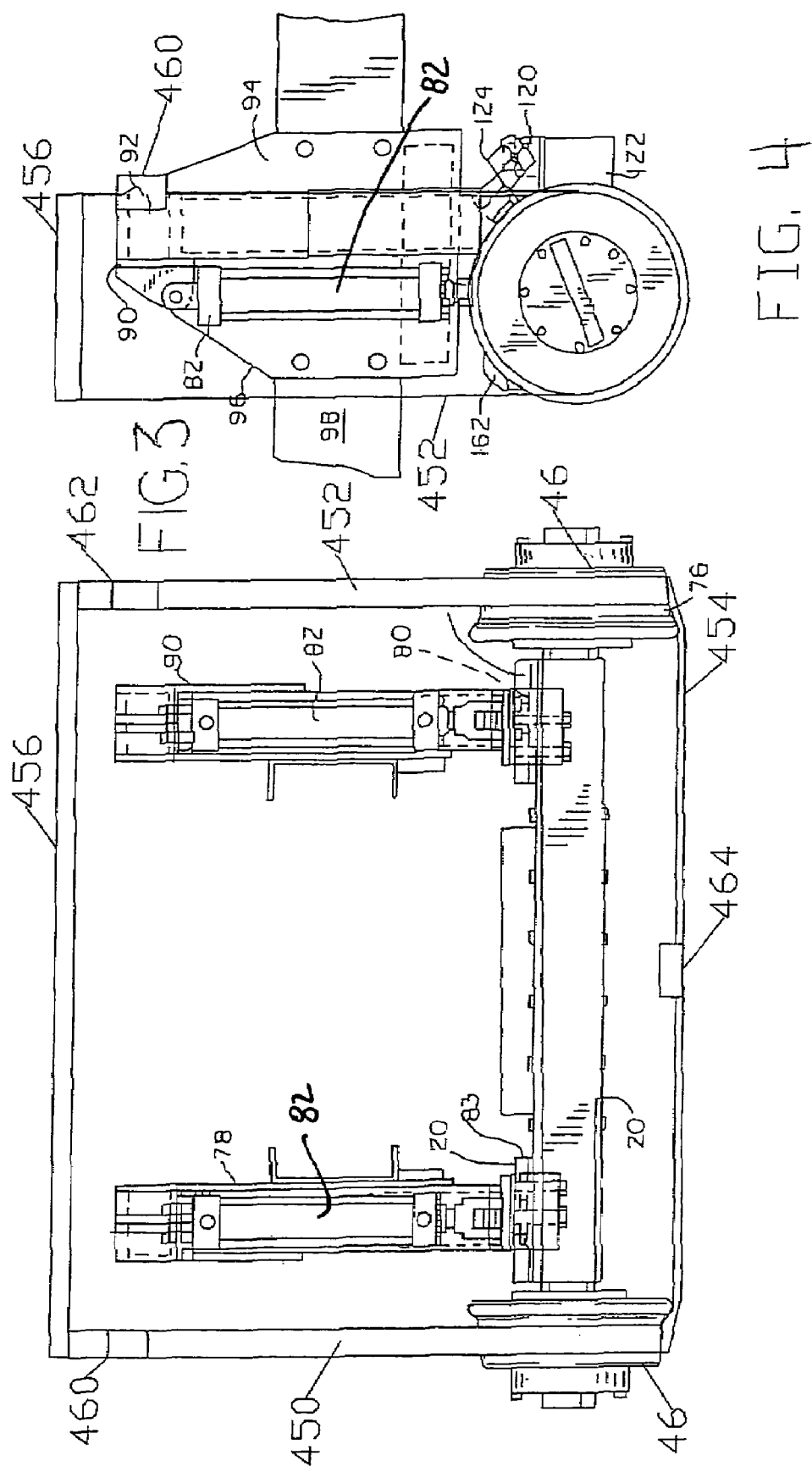

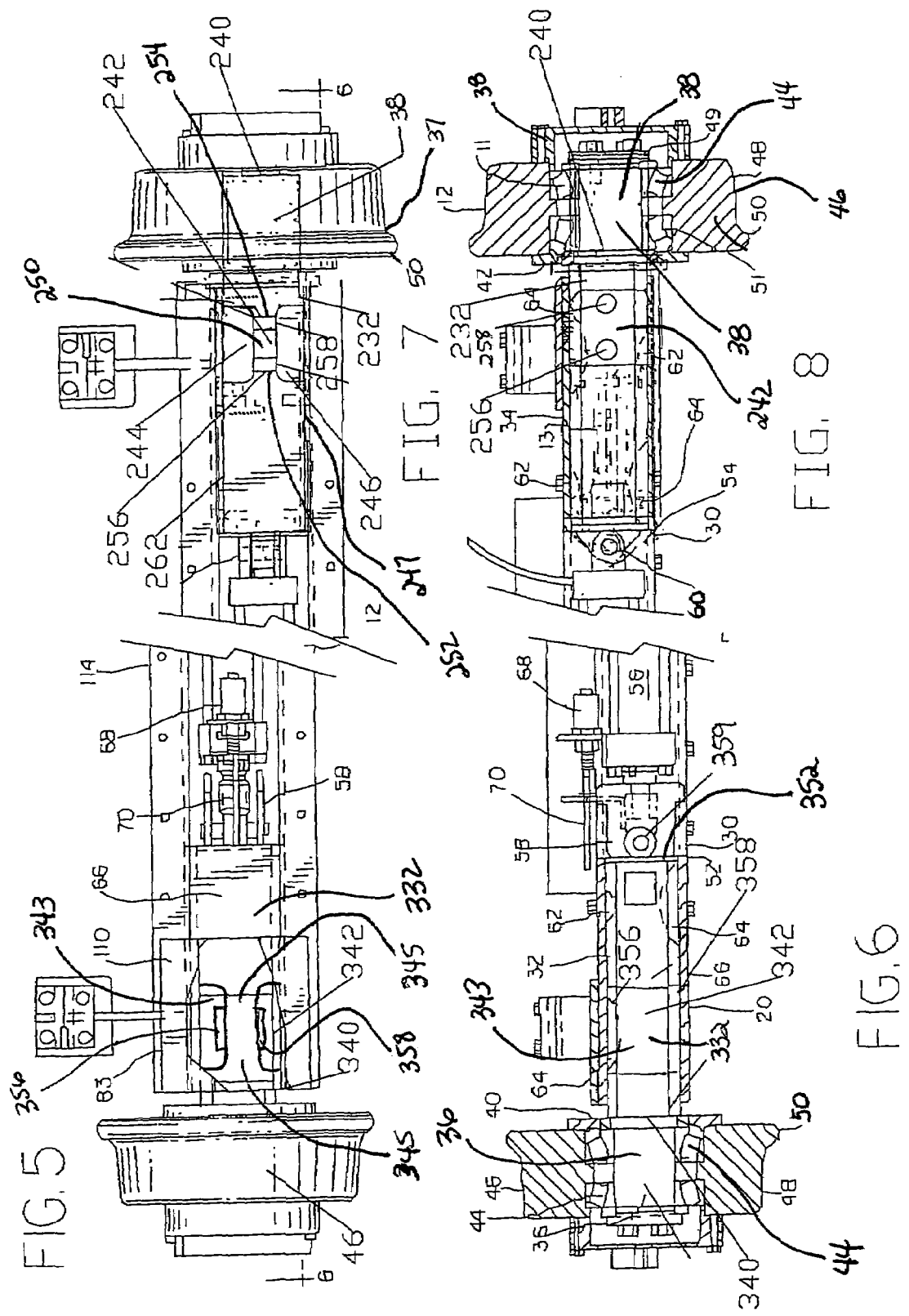

GAUGE RESTRAINT MEASUREMENT SYSTEM

This divisional application claims priority from U.S. patent application Ser. No. 10/749,716 filed Dec. 31, 2003, now U.S. Pat. No. 7,007,561 which claims priority from U.S. Provisional Application Ser. No. 60/437,467 filed Dec. 31, 2002.

BACKGROUND

This disclosure relates to improvements in measurement and calibration of apparatus used for testing the track strength of railroad track, tie and fastener conditions using a loaded gauge axle assembly which imparts a calibrated downward force and a calibrated outward force on the rails, and measures the load applied to the rails to determine the strength of the rails, ties and fasteners.

By way of background but not limitation, various types of measurement and calibration devices are utilized by the industry for testing strength of railroad tracks, ties and fasteners including a "Gauge Restraint Measurement System (GRMS)" from the U.S. Department of Transportation also described in an article entitled "AAR's Track Loading Vehicle" and U.S. Pat. No. 5,756,903 issued May 26, 1998. The teachings of said U.S. Pat. No. 5,756,903 are incorporated by reference as if fully set forth herein.

The track strength testing vehicle of U.S. Pat. No. 5,756,903 measures changes in hydraulic fluid pressure to determine both changes in load due to track strength changes and to control the load applied.

This system introduces potential error in the measurements because of factors such as time lag between changes at the wheel and measurement of pressure, errors introduced by pressure changes made to preserve load at the wheel, and the number of components, instruments and calculations involved. This system does not account for frictional forces within the split-axle assembly and cannot be used as a true rail/wheel force through direct transducer measurement.

While the track strength testing taught in U.S. Pat. No. 5,756,903 is believed to be reliable and cost effective, its measurement system is believed to be somewhat over-inclusive, in that the statistical variations result in indications of track failure, when in fact the track is within specifications. Improved accuracy, therefore, can be expected to have economic and time saving benefits in minimizing unnecessary repairs, and operational benefits in the ability to reliably and rapidly locate those areas in need of repair.

The testing apparatus of U.S. Pat. No. 5,756,903 is a significant improvement over the very large sized competitive track testing machines in that the load gauge axle assembly can be comparatively easily removed and replaced, both for maintenance, and also for calibration. Under the arrangement of U.S. Pat. No. 5,756,903 complete calibration is accomplished by removal of the axle assembly and testing in a laboratory or shop. Field calibration can only be accomplished on certain components and systems. Rail car mounted testing apparatus, or track maintenance apparatus the size and mass of rail cars are even more difficult to calibrate, as the size of the vehicle and its components essentially requires removal from service and return to a shop.

In view of the above, it should be appreciated that there is a need for a device that accurately measures track strength and permits expedient calibration of the measurement device. The present disclosure satisfies these and other needs and provides further related advantages.

SUMMARY

The disclosure comprises a direct measuring loaded gauge axle assembly that measures track strength by directly measuring loads on split axles as vertical loads are imposed by hydraulic rams. Horizontal loads are supplied by a horizontal ram through split axles and flanged steel wheels to the rail head of the railroad tracks, enabling improved calibration to measure track strength and electronic data recording and comparison.

Other features and advantages of the disclosure will be set forth in part in the description which follows and the accompanying drawings, wherein the embodiments of the disclosure are described and shown, and in part will become apparent upon examination of the following detailed description taken in conjunction with the accompanying drawings.

BRIEF DESCRIPTION OF THE DRAWINGS

The above mentioned and other features of this disclosure and the manner of obtaining them will become more apparent and the disclosure will be best understood by reference to the following description of embodiments of the disclosure taken in conjunction with the accompanying drawings in which:

FIG. 1 is a side elevational view of the motor vehicle and loaded gauge axle track strength apparatus on a railroad track;

FIG. 2 is a top plan view of the motor vehicle body and loaded gauge axle track strength apparatus with the body portion in section to show the arrangements;

FIG. 3 is a front elevational view of the loaded gauge axle track strength apparatus with the calibration assembly with the calibration subsystem;

FIG. 4 is a left side elevational view of the loaded gauge axle track strength apparatus with the calibration subsystem;

FIG. 5 is a top plan view of a first side of the prior art loaded gauge axle track strength with the load cell sensor embodiment;

FIG. 6 is a front sectional view of a first side of the prior art loaded gauge axle track strength apparatus with the load cell sensor embodiment;

FIG. 7 is a top plan view of a second side of the loaded gauge axle track strength apparatus;

FIG. 8 is a front sectional view of a second side of the loaded gauge axle track strength apparatus;

DETAILED DESCRIPTION

Figure 9:
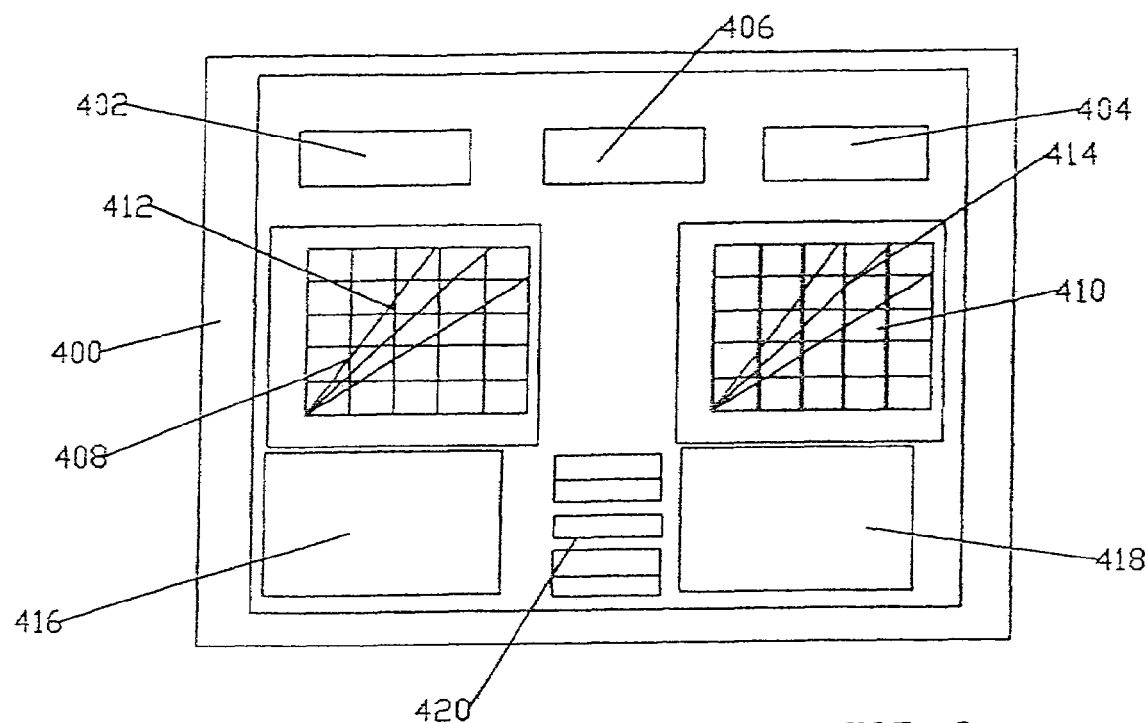
FIG. 9 is a display of the data collected by the loaded gauge axle track strength apparatus.

While the present disclosure will be described fully hereinafter with reference to the accompanying drawings, in which a particular embodiment is shown, it is to be understood at the outset that persons skilled in the art may modify the disclosure herein described while still achieving the desired result. Accordingly, the description that follows is to be understood as a broad informative disclosure directed to persons skilled in the appropriate art and not as limitations on the present disclosure.

As illustrated in the drawings, the truck vehicle 10 has road wheels 12 and high rail wheels 14. This arrangement enables operation of the vehicle on ordinary roads, driving to railroad tracks 16 and straddling them, then actuating the retractable high rail wheels 14 to partially lift the truck off the rails 17. Motive drive is nevertheless still provided with the road wheels through the rubber tires 18. Gauge axle assembly 20 is located between the truck wheels 12.

The high rail units 14 are preferably forward of the front end 22 and rearward of the rear end 24 of the vehicle, forward of the front end 22 on a front frame extension 26 and rearward of the rear end 24 on a frame extension 28, as shown in FIG. 1.

The gauge axle assembly 20 is used to apply a calibrated side load on the tracks 16. Variation in track side load is measured by the gauge axle assembly 20 and the measurements taken are analyzed to determine the strength of the track 16 by measuring variations in hydraulic pressure as load is also placed on the gauge axle. Split axle assembly 30 made up left and right generally square sectioned shafts 32, 34 each having a spindle 36, 38 on its outboard end 40, 42, as generally discussed in U.S. Pat. No. 5,756,903 and as shown in FIGS. 6 and 8.

Spindles 36, 38 and bearings 44 have wheels 46. Wheels 46 have surfaces 48 that diverge toward flange 50. Bearing races 49 and 51 in the wheel 46 and on the spindles 36, 38 have thrust and support surfaces.

At the inboard ends 52, 54 a hydraulic ram 56 is attached to clevis and pin fittings 58, 60. Ram 56 provides the outward force necessary for the flange 50 of the wheel 46 to maintain contact with the head 19 of the tracks 16. Shafts 32, 34 are carried on ultra high molecular weight (UHMW) plastic slides 62, 64 in housing 66.

An improvement in this application, compared to U.S. Pat. No. 5,756,903 is in major measurement improvements enabled by new split axle shafts 232, 234, or 332, 334 that incorporate force sensors positioned on the shafts.

As described in the aforementioned patent, distortion or variation in hydraulic pressure is directly measured by a linear transducer on the hydraulic line pressurizing ram 56. Track strength is then calculated by comparing the measured pressure under a constant lateral load to an unloaded gauge measurement and a delta gauge or a rail movement is computed. Because this system measures fluid pressure, there is a slight time lag in obtaining reading, rendering it difficult to accurate log measurements. Certain inaccuracies in the system occur due to physical properties of hydraulic fluid and friction in the hydraulic system, which results in a greater deviation in the numbers calculated than desired.

In order to have a substantially constant load applied to the wheels 46 in the prior art systems, hydraulic pressure in the hydraulic ram 56 needs to be constantly adjusted. When a track weakness, caused by rail, tie or fastener failure, permits the wheels 46 to move, movement of the hydraulic piston in the hydraulic ram 56 causes the volume in the hydraulic system to increase, decreasing fluid pressure in the system. To compensate for movement of the piston of the hydraulic ram 56, system hydraulic pressure is increased by the controls.

When the track returns to a gauge closer to the desired mean gauge in the specification, there is a consequent decrease in volume in the cylinder of the hydraulic ram 56, increasing fluid pressure in the system. To compensate for movement of the piston of the hydraulic ram 56, system pressure is reduced by the controls. Compensation in the system for fluxation in pressure creates a large disparity in the resultant measurements.

Figure 10:
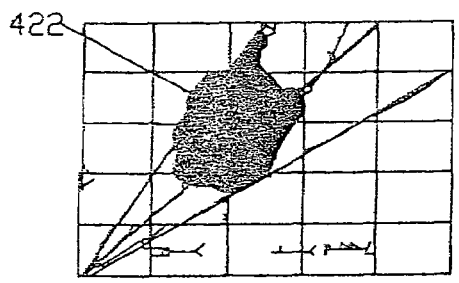
FIG. 10 is a plot of results from the prior art load loaded gauge axle track strength apparatus.
Figure 11:
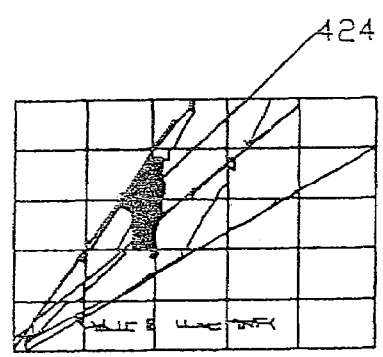
FIG. 11 is a plot of results from the improved loaded gauge axle track strength apparatus.

Because of the great deviation, caused by the fluxation in cylinder volume, railroads unnecessarily stop and physically inspect track that in fact is within specification, which reduces the efficiency of maintenance operations and increases maintenance costs. These plots of the open loop hydraulic system utilizing force measurements taken off of the hydraulic system are shown in FIG. 10. The more accurate results of the improvement, described below, are shown in FIG. 11.

The present disclosure addresses these undesirable traits by using direct mechanical measurement of changes in load or strain in split axle shafts 232, 332 as shown in FIGS. 5-8. The axle assembly measures changes in load or strain in each of the split axle shafts 232, 332. The axle assembly 20 applies a lateral load by use of hydraulic ram 56 and applies a vertical load with use of hydraulic cylinders 82. The axle assembly 20 will be described regarding one side of the loaded gauge axle assembly 20, it being understood the other side is a mirror image. Shaft 232, of the first embodiment of the present disclosure, uses load cells 256, 258 while shaft 332, of the second embodiment of the present disclosure, uses strain sensors 356, 358. Either the strain sensors 356, 358 or the load cells 256, 258 provide essentially instantaneous measurement of changes in load on the split axle shafts 232, 332. The installation of force transducers, such as the load cells 256, 258 in the cantilevered section of the split axle shafts 232 or 332 outside of the frictional elements of the axle assembly 20 subjects the load cells 256, 258 to rail/wheel forces and not frictional forces created by the hydraulic ram 56. The avoidance of frictional forces at the measurement point permits a more accurate detection of lateral weakness in the analyzed track.

Vertical and lateral forces placed upon the track are separately and independently, measured by the load cells 256, 258. The direct force vertical and lateral measurement in the non-rotating split axle shafts 232 is continuous along the running track. The orientation of the load cells 256, 258 within each of the split axle shafts 232 determines whether the analog output load cells 256 will be lateral load output or vertical load output. The load cells 256, 258 are designed so that the orientation of the load cell within an opening determines whether the forces measured are lateral or vertical. The load cells include alignment markings wherein the orientation of the markings dictates the type of force measured. Positioning the alignment markings in a vertical orientation allows the load cells to measure lateral force and positioning the alignment markings of the load cells forty five degrees from vertical permits the load cells to measure vertical force. While orienting load cells within the split axle shafts 232 in the described configuration is the preferred method of measuring forces in the split axle shafts 232, other configurations of the load cells for measuring lateral and vertical forces may also be used to achieve the same result. Further, other possible force measuring devices that may be used to measure vertical and lateral forces within the split axle shafts 232.

Split axle shaft 232 includes a spindle 36 at the outboard end 240 as shown in FIG. 8. The spindle is adapted to accept bearings 44 and wheel 46. Wheel 46 includes surfaces 37 that diverge toward a flange 50. The wheel 46 and flange 50 are positioned on the head 19 of the rail 16. Bearing races 49 and 51 in the wheel 46 and on the spindles 36, 38 have thrust and support surfaces to prevent lateral and vertical play between the wheel 46 and the split axle shaft 232. The use of bearings 44 permits the wheel 46 to rotate along the track while the split axle shaft 232 remains stationary. This is necessary so that the orientation of the load cells 256, 258 remain constant.

At the inboard end 252 of each of the split axle shafts 232 the hydraulic ram 56 is attached by clevis and pin fittings 58, 60. The hydraulic ram 56 is expanded and contracted by varying pressure on both ends of the cylinder within the hydraulic ram 56 in response to signals from the load cells 256, 258. The hydraulic ram 56 is designed to pull and push the split axle shafts 232 so that a constant force is applied to the tracks. Using a closed loop system, as described below, a substantially constant lateral force and a substantially constant vertical force in an allowable range set by the FRA for GRMS measurement is applied to the tested track.

Figure 13:
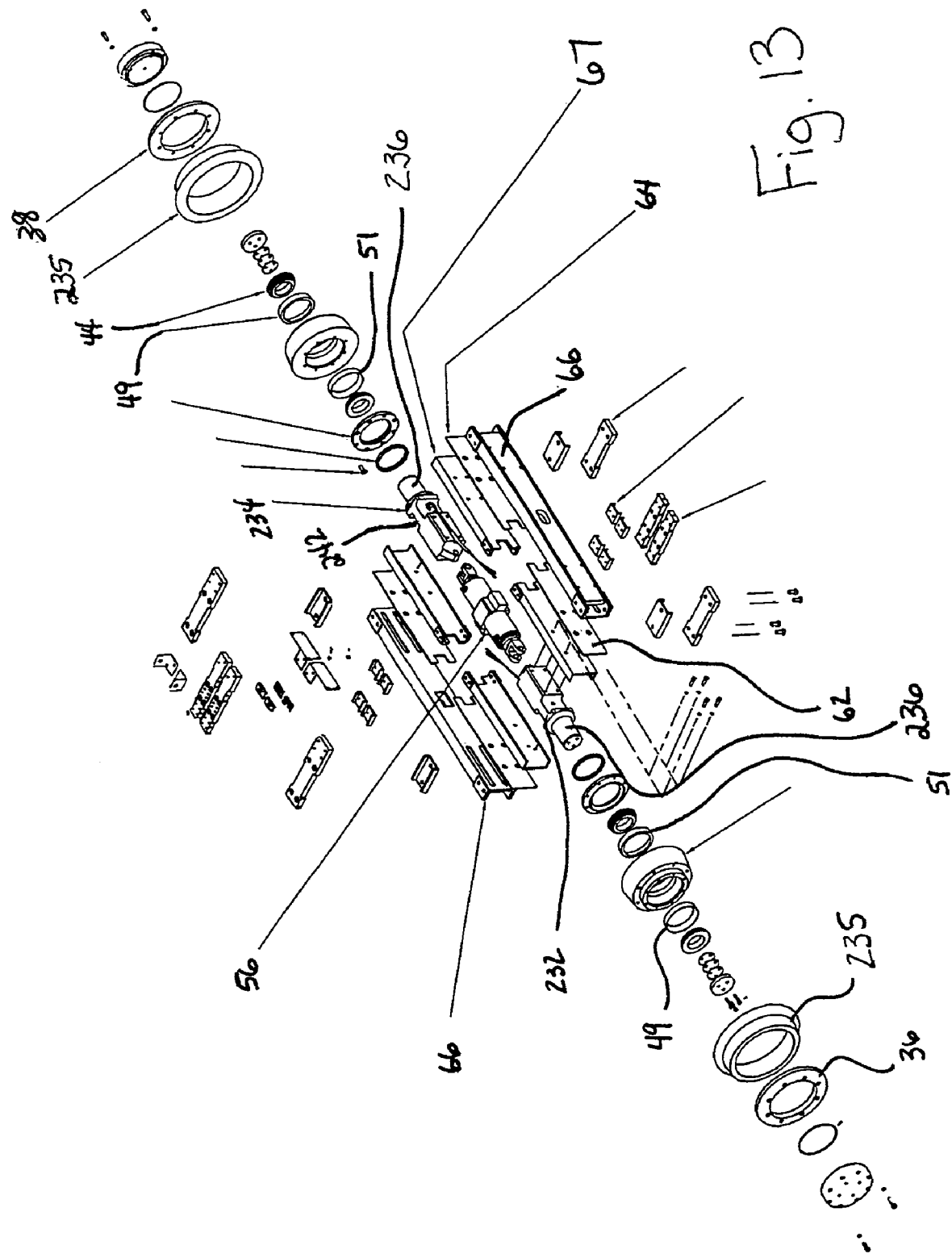
FIG. 13 is an exploded view of the loaded gauge axle track strength apparatus.

The split axle shafts 232 are located at opposite ends of the hydraulic ram 56 and are slidably disposed within a housing 66, as shown in FIG. 13. One skilled in the art will recognize that FIG. 13 is merely a clarification of the axle assembly 20 of FIGS. 3-8. The housing 66 includes inner support channels 67, wherein the inner support channels 67 slide with respect to the housing 66. The inner support channels 67 are secured to the split axle shafts 232. To permit movement of the inner support channels 67 with respect to the housing, ultra high molecular weight (UHMW) plastic slides 62, 64 are used.

Spaced in from end 240 of the split axle shaft 232 is a load sensing region 242, as shown in FIGS. 7 and 8. In the first embodiment, utilizing load cells 256, 258, load sensing region 242 is machined or formed to define two opposed recesses 244, 246 in side surfaces 247 of the split axle shafts 232. The recesses 244, 246 are vertically formed, so that the full height of split axle shaft 232 is intact, but the width is reduced by about sixty percent, each recess having a depth of about 30 percent, with the remaining solid portion forming a web 250 comprising about 40 percent of the width of split axle shaft 232.

The web 250, positioned between the recesses 244, 246, is itself bored to provide two apertures 252, 254 to receive load cells 256, 258, for which the leads 260 are lead away from the apertures in groove 262 to protect the wiring for the load cells 256, 258 as shown in FIG. 7. During the application of lateral and vertical forces by hydraulic ram 56 and cylinders 82, the apertures 252, 254 slightly deform, exerting pressure on the load cells 256, 258. The force exerted on the load cells 256, 258 is translated into analog signals that are transmitted to a signal conditioning amplifier.

The load cells 256, 258 are tubular members that are adapted to measure force applied to their structure. The load cells 256, 258 are designed so that their orientation within the apertures 252, 254 determine whether the output for a given cell relates to vertical or lateral load. To measure lateral force on the split axle shaft 232, the alignment markings of the load cell 256 are positioned in a vertical orientation within the aperture 252. To measure vertical force on the split axle shaft 232, the alignment markings of the load cell 258 are positioned forty five degrees from vertical. The load cells 256, 258 continuously measure lateral and vertical force applied to the rails, the values of which are recorded. While orienting load cells within the split axle shafts 232 in the described orientation is the preferred method of measuring forces in the split axle shafts 232, other configurations of the load cells for measuring lateral and vertical forces may also be used to achieve the same result.

In the second embodiment, using strain sensors 356, 358, shaft 332 includes a spindle 36 at the outboard end 340 of the split axle shaft 332. At the inboard ends 352 the hydraulic ram 56 attaches to clevis and pin fittings 359. Spaced in from end 340 is a load/strain region 342. The load/strain region 342 is created by creating opposing recesses 343 within the split axle shaft 332. Between the recesses 343 is a central web 345. It is preferable that the central web portion 345 be approximately ½" in thickness. In the second embodiment, the central web portion 345 of the load/strain region 342 is surface fitted with strain sensors 356, 358, which transmit strain information to the control system. The strain sensors 356, 358 can be attached to the surface of the central web portion 345 with adhesive, fasteners or welding. The compression or shear deformation of the central web portion 345 is measured by the strain sensors, creating an analog signal sent to the signal conditioning amplifier. The strain information detected by the strain sensors 356, 358, permits the control system to monitor load force on the split axle shafts 332 and vary hydraulic pressure within the hydraulic ram 56 to compensate for movement in the track.

Due to the unique advantages of the non-rotating split axle embodiment taught herein and in U.S. Pat. No. 5,756,903, either load sensors 256, 258 or strain sensors 356, 358 can be used to directly measure load/strain on the axle, in a selected direction. Competitive track strength testing vehicles with rotating axles cannot be easily adapted to use of load/strain measurements because of the difficulty of identifying the direction of load/strain as the axle rotates. The direct force measurement in the non-rotating axle shaft 332 is continuous along the running rail.

The lateral and vertical force control of the gauge restraint measurement system is a closed-loop control system that is capable of making continuous changes in force exerted by the hydraulic ram 56 in response to force readings provided by the load cells 256, 258. This arrangement ensures that a constant force is continuously applied to the track as the gauge restraint measurement system is rolling down the railway at speeds varying from 5 mph to 35 mph. It is essential to apply a constant lateral and vertical force upon the tracks even while the tracks are moving in response to the force so that an accurate and consistent measurement of variations in gauge, hence lateral strength of the track can be measured to show the extent of lateral weakness of the track. As the test vehicle encounters a laterally weak section in the track, the track moves in response to the forces, decreasing the load on the load cells. In response to the decrease in force, the hydraulic ram 56 expands increasing the force on the track until the desired force is achieved. Without the increase in force, accurate track gauge measurements could not be made.

The closed loop hydraulic control system is designed to maintain a constant rail/wheel lateral force. This is accomplished by use of a hydraulic servo-valve controlled by force feedback provided by force transducers, load cells 256, 258, in the extremity of the split axle shaft 232, closest to the wheel. Using the closed loop system, pressure on the rail does not drop with movement of the track. To maintain constant pressure on the tracks, the hydraulic servo-valve is used to rapidly increase pressure on either side of the hydraulic ram 56. In the preferred embodiment a Moog 72-102 servo valve is used to supply pressurized fluid to either end of the hydraulic ram 56. The servo-valve includes a first hydraulic line that connects to a first end of the hydraulic ram 56, and when pressurized, causes the ends of the hydraulic ram 56 to move outward exerting additional pressure on the split axle shafts 232. Pressurizing the first hydraulic line, causes the extension of the hydraulic ram 56 and the extension of the overall length of the axle assembly 20, which compensates for outward movement of the track. The servo-valve also includes a second hydraulic line that connects to a second end of the hydraulic ram 56, and when pressurized, causes the ends of the hydraulic ram 56 to pull inward, decreasing pressure on the split axle shafts 232. Pressurizing the second hydraulic line causes the retraction of the hydraulic ram 56 and an overall decrease in the length of the axle assembly 20 to compensate for lack of track movement, i.e. standard track gauge within specifications.

The servo-valve is controlled by the system computer in response to signals received from the load cells 256, 258. If the load cells 256, 258 send a signal showing a drop in force on the track, due to track lateral weakness, the computer sends an analog signal to the servo-valve to increase hydraulic pressure in the first end of the hydraulic ram 56, maintaining constant force on the split axle shafts 232 and expansion of the overall length of the axle assembly 20. If the load cells 256, 258 send a signal showing an increase in force on the track, due to the transitioning from a weak section of track to a strong section of track, the computer sends an analog signal to the servo-valve to increase hydraulic pressure in the second end of the hydraulic ram 56, maintaining a constant force on the split axle shafts 232, reducing the overall length of the axle assembly 20. The closed loop force control system has a fast response time that effectively reacts to changes in track conditions. The closed loop system pushes the split axle shafts 232 outward and pulls the split axle shafts 232 inward to create a uniform load on the track. This arrangement creates a highly constant force on the track, permitting highly accurate track strength measurements.

To measure physical changes in distances between the rails of the track being tested in the preferred embodiment, a laser measurement system is used. While a laser measurement system is utilized, other means for measuring may also be incorporated such as mechanical means. The front of the track strength testing vehicle is equipped with an inspection camera and laser measurement device to measure unloaded gauge. The laser measurement device at the front of the vehicle takes a pre-force distance measurement of the track in an unstressed state. The measurement data is sent to and recorded by the system computer. A second inspection camera and laser measurement device is mounted under the vehicle adjacent to the load axle 20, and is adapted to measure the distance between the rails of the track being tested under load. The values collected by the second laser measurement device are recorded by the system computer. The computer compares the differences between the first and second measurements and records the difference. The difference in the track gauge between a loaded and unloaded state in combination with the associated forces is used to determine whether a section of track is in need of repair.

The direct measurement of load/strain on the split axle shafts 232 themselves enables the track strength testing vehicle to acquire and store load axle force data and provide a graphical display that is used for the evaluation of the gauge restraint measurement system GRMS load axle performance during revenue service. In addition to the features described in U.S. Pat. No. 5,756,903 and the improvements described above, this improvement utilizes a computer used for the load cell calculations, including signal amplification and A/D cards.

Lateral and vertical load values are calculated by the load cell computer from input from the load cells 256, 258. The load cell computer used for the load cell calculations uses converter boards to convert amplified and conditioned analog signals developed by the load cell circuitry to digital values (A/D converter boards). The signal conditioner boosts the analog signal from the load cells 256, 258. The A/D boards covert the amplified analog signal to a digital signal. The A/D converter board values can be used for force calculation purposes. The calculated lateral and vertical load values are used as digital inputs to the program.

The three cameras used in the system have one camera positioned to send video of the track directly ahead of the track strength testing vehicle. This video is used to correlate track conditions with graphical results produced by the program. The video also allows for custom graph production during playback mode. The two other cameras used in the system send video that allows monitoring load axle wheel performance in a loaded and unloaded state and the lateral and vertical position of the load axle with respect to the vehicle. An illustration of the display 400, is shown in FIG. 9.

Camera graphics show the left wheel, 402, right wheel 404 and outside environment 406. Data plots on the left, drivers side, 408 and right side 410 show the progression of data collection and plot points in a 'scatter plot' form relative to statistical envelopes 412, 414. Corresponding histograms 416, 418 provide a different statistical view of the data points. Finally, in the preferred embodiment, an array 420 of computer control 'buttons' is in the lower center of the display 400.

Typical computer controls will be used to operate the system, including start, reset, pause and resume functions, in addition to various data field entry. The controls are used for such functions as skipping curves, switches, frogs, constructing custom graphs to show tangent behavior only or curve behavior only.

A primary function of the system is that of graph-building and retaining accumulated graphed data, correlated to the odometer and track location video. The graphs plot data points for left and right rails, displaying the data points as accumulated plots with applied vertical force on the "y" axis and applied horizontal force on the "x" axis. Also displayed are the limits of permissible deviation of the "x" and "y" values from an 'envelope' of acceptable force. The general display is shown in FIG. 9, while a comparison of data plots in the prior art loaded gauge axle track strength apparatus compared to the improvement, both using the computer monitoring system described above, are shown in FIG. 10 and FIG. 11, respectively.

The system allows the operator to view a two-dimensional graph of lateral and vertical forces displayed on a computer monitor. A two-dimensional scatter-graph is displayed for each wheel showing a dot for each foot of travel along the running rail. Dots are positioned on the graph with later position relative to the horizontal scale and vertical position relative to the vertical scale calibrated in kips (thousands of pounds). A third dimension is added by color graduation of the scatter-graph according to frequency of occurrence. Thus, the graphical display showing a degree of force control effectiveness is made available to the operator (and customer). The resulting display is not unlike a weather-radar image that illustrates different colors for variations in rain density/intensity. Graphical force distribution information is made available to the operator so that he can monitor control system performance. By visually monitoring the force distribution scatter-graph, the operator can detect control system degradation over time and take corrective action. Pattern recognition enables an operator to identify a developing problem at the component level, which greatly enhancing the maintainability of the system and the availability of the system to produce revenue, resulting in significant economic benefit for the operator and better service to the customer.

Experimentation has shown the interrelation between the load/strain sensor arrangement and the plots described above. With the prior art hydraulic pressure sensing surrogate for the mechanical properties, points were more frequently outside the permissible 'envelope' as shown in FIG. 10. This plot is created using an open loop force control apparatus, and it is for this reason it is designated as "Prior Art." In fact, however, the display apparatus is that of the improvement as to display and calculations discussed herein. Using the closed loop control system, greater precision and fewer false indications of inadequate strength are received. This is shown in FIG. 11. It will be observed that the data points plotted 422 using the open loop system covers a much larger area of the graph than plot 424, using the closed loop system.

The track strength measurement system can be quickly calibrated without the need to send the system to an independent laboratory that could take a measurement vehicle offline for several weeks, causing loss in revenue. Accordingly, an additional feature of the track strength measurement system is the Load Axle Calibration Subsystem, hereafter sometimes abbreviated "LACS".

The purpose of the LACS application is to automatically increment vertical and lateral hydraulic pressures in a planned sequence while simultaneously acquiring load axle load cell force data and comparing to permanently installed NIST traceable transfer standard load cells 460, 462, hereinafter referred to as transfer standard cells, in order to generate correction constants for the load cell correction application as a field calibration procedure, as shown in FIGS. 3 and 4. This self-contained system directly compares the transfer standard cells 460, 462 with the force measurement signals generated by the internal load-axle load cells and establishes a linear mathematical relationship that is stored in the measurement system computer. The system utilizes the transfer standard cells 460, 462 that independently measure the force applied to the wheels 46 by the hydraulic cylinders 82. The transfer standard cells 460, 462 can be removed from the vehicle and sent to a testing center to ensure their accuracy. A spare set of transfer standard cells 460, 462 can be retained so that the vehicle is not out of service. Typically the transfer standard cells 460, 462 need to be calibrated once a year to ensure accuracy.

The entire calibration procedure of the load axle 20 takes approximately 10-15 minutes. The application automatically installs calibration constants for the load cell correction application and prints a calibration report for distribution to the customer.

The LACS system utilizes vertical polyester web straps 450, 452 to support wheels 46 and a lateral polyester web strap 454 to restrict lateral movement of the wheels 46 as shown in FIGS. 3 and 4. While polyester web straps are preferred, other types of material and harnesses may be used to restrict vertical and lateral movement. A centering device is incorporated on top of the load axle 20 during calibration to center the axle ensuring vertical loading. Vertical loads are sensed by transfer standard cells 460, 462 and lateral loads are sensed by transfer standard cell 464. The vertical load cells 256 are tested by use of transfer standard cells 460, 462. The calibration procedure can be performed in a hotel parking lot prior to starting the track testing work day.

To calibrate the system, the operator places the vertical polyester web straps 450, 452 over the wheels 46 and connects the ends of the polyester web straps 450, 452 to a transfer standard cell support bracket 463. A separate support bracket 456 is directly connected to a first end of each of the transfer standard cells 460, 462. The transfer standard cells 460, 462 are connected to the vehicle at a second end. Once the polyester web straps 450, 452 are in position around the wheels 46, the hydraulic cylinders 82 are expanded incrementally to test vertical load cells 256. The hydraulic cylinders 82 are moved downward with ten increments of increasing force. The test begins with a load of 2,000 lbs vertical force applied to the split axle shafts 232 and moves upward in ten equal increments until 15,000 lbs of vertical force is achieved. The vertical force values detected by the transfer standard cells 460, 462 are compared to the vertical force values detected by the load cells 256. If the vertical force measured from the load cells 256 varies from the vertical force measured by the transfer standard cells 460, 462, the load cells 256 are recalibrated to match the values of the transfer standard cells 460, 462.

To calibrate lateral load force, a polyester web strap 454 is attached to the wheels 46 by use of brackets to restrict lateral movement of the wheels. The transfer standard cell 464 is fitted to the lateral polyester web strap 454 so that an independent lateral load can be detected. Once the lateral polyester web strap 454 and transfer standard cell 464 are in position, the hydraulic ram 56 is expanded in 10 equal increments from 2,000 lbs to 9,000 lbs so that test values can be gathered. The lateral force values measured by the transfer standard cell 464 are compared to the lateral force values measured by the load cells 258. The analog signal from the load cells 258 are assigned a numerical force value, which is compared to the output reading of the transfer standard cell 454. If the lateral force value gathered from the load cells 258 varies from the lateral force output reading of the transfer standard cell 454, the values assigned to the output of the load cells 258 are recalibrated to match the load values of the lateral strains sensor 454. The NIST transfer standard cells 460, 462, 464 are calibrated annually to maintain traceability for GRMS system calibration and performance.

Calibration files are retained and used to maintain a historical statistical quality assurance graph for the detection of gradual or abrupt system changes. The statistical quality assurance graph is used as a maintenance and monitoring tool by both field crew and engineering staff as a maintenance and design decision making tool.

In the preferred embodiment, the calibration subsystem uses a cPCI QNX processor and cPCI analog/digital A/D converter in 3U Eurocard chassis. This will be operatively connected to a server used for the host program including A/D cards and D/A cards. Measurements are provided by transfer standard cells from Sensotec model AL416EL or similar from Omega Engineering.

The LACS hardware 500 to support the transfer standard cells 460, 462, 464 will be mounted beneath the truck body above the load axle wheels as shown in FIGS. 3 and 4. Signal conditioning will be used for the three tertiary standard load transducers to amplify the analog signals from the load transducers.

Figure 12:
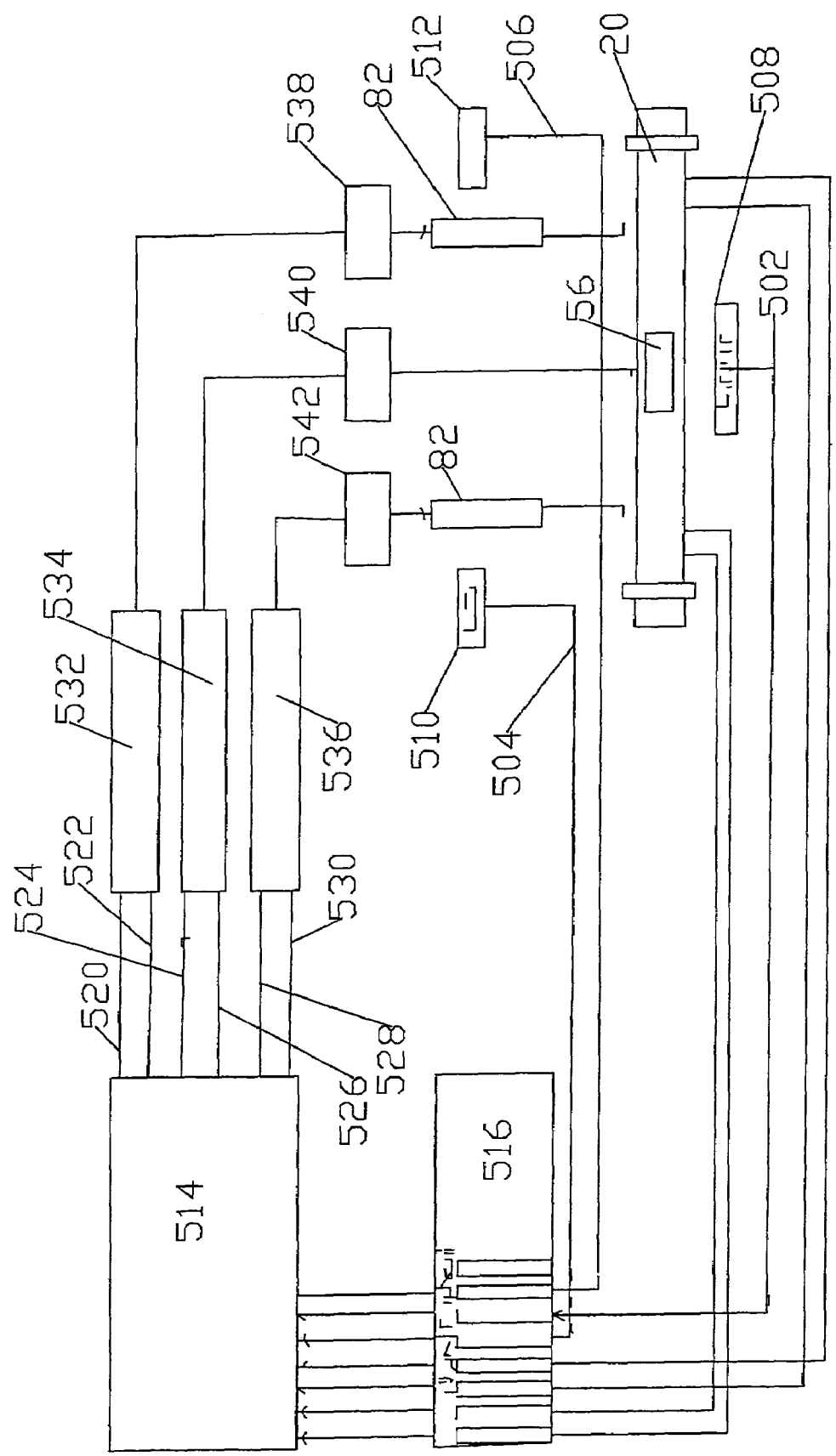
FIG. 12 is a flow chart of the load axle calibration subsystem.

Lateral 502, and vertical force values 504, 506, from transfer standard cells 460, 462, 464 are fed from the three signal conditioner amplifiers 508, 510 and 512 into three available channels of the LC computer A/D card as shown in FIG. 12. The cPCI computer 514 used for the load cell calculations uses an A/D converter to convert analog signals developed by the axle load cell circuitry to digital values that can be used for force calculation purposes. These raw lateral and vertical force values are fed through the signal conditioner 516 and then directly through the load cell computer 514 as uncorrected values and used as digital inputs to the calibration program running on the host computer.

As the calibration operation is performed, progress of the test procedure, verification of performance within specifications or failure, and documentation of identification, time, specification and reporting of same will be displayed and provided.

Various features of the disclosure have been shown and described in connection with the illustrated embodiment, however, it is understood that these arrangements merely illustrate, and that the disclosure is to be given its fullest interpretation.

What is claimed is:

1. A method for monitoring track strength comprising the steps of:
   receiving analog signals from force sensors positioned on axle half shafts of a rail strength measuring axle;
   boosting the analog signals from the force sensors;
   converting the analog signals from the force sensors to digital values;
   calculating lateral and vertical load values based on the digital values;
   providing a graphical display of the lateral and vertical load value data points; and
   displaying the limits of permissible deviation of values from an envelope of acceptable force;
   further including the step of increasing hydraulic force on the rail strength measuring axle when the lateral load value is below a predetermined level to maintain a constant lateral force on the tracks.

2. A method for monitoring track strength comprising the steps of;
   receiving analog signals from force sensors positioned on axle half shafts of a rail strength measuring axle;
   boosting the analog signals from the force sensors;
   converting the analog signals from the force sensors to digital values;
   calculating lateral and vertical load values based on the digital values;
   providing a graphical display of the lateral and vertical load value data points; and
   displaying the limits of permissible deviation of values from an envelope of acceptable force;
   further including the step of decreasing hydraulic force on the rail strength measuring axle when the lateral load value is above a predetermined level to maintain a constant lateral force on the tracks.

3. A method for monitoring track strength comprising the steps of:
   receiving analog signals from force sensors positioned on axle half shafts of a rail strength measuring axle;
   boosting the analog signals from the force sensors;
   converting the analog signals from the force sensors to digital values;
   calculating lateral and vertical load values based on the digital values;
   providing a graphical display of the lateral and vertical load value data points; and
   displaying the limits of permissible deviation of values from an envelope of acceptable force;
   further including the step of increasing the vertical hydraulic force on the rail strength measuring axle when the vertical load value is below a predetermined level to maintain a constant vertical force on the tracks.

4. A method for monitoring and controlling lateral and vertical forces applied to a medium being tested, the method for monitoring and controlling the lateral and vertical forces on the tested medium comprising the steps of:
   receiving analog signals from force sensors positioned within a force application device;
   boosting the analog signals from the force sensors;
   converting the analog signals from the force sensors to digital values;
   calculating lateral and vertical load values based on the digital values;
   increasing or decreasing lateral and vertical forces on the tested medium to maintain a substantially constant lateral and vertical force on the tested medium;
   providing a graphical display of the lateral and vertical load value data points; and
   displaying the limits of permissible deviation of values from an envelope of acceptable force.

5. The method for monitoring and controlling lateral and vertical forces of claim 4 further including the step of receiving video signals from cameras monitoring the tested medium.

6. The method for monitoring and controlling lateral and vertical forces of claim 5 further including the step of storing the video signals.

7. The method for monitoring and controlling lateral and vertical forces of claim 4, further including the steps of receiving and storing input received from an electronic measuring device.

8. The method for monitoring and controlling lateral and vertical forces of claim 4, further including the steps of receiving and storing input received from a electronic counter and associating the counter reading to the lateral and vertical load values.

9. The method for monitoring and controlling lateral and vertical forces of claim 4 wherein the force sensors are in the form of load cells to detect changes in lateral and vertical forces in the force application and detection device.

10. The method for monitoring and controlling lateral and vertical forces of claim 4 wherein the force sensors are in the form of strain gauges used to detect changes in lateral and vertical forces in the force application device.

11. A method for monitoring and controlling forces applied to a medium being tested, the method comprising the steps of:
    receiving analog signals from force sensors positioned within a force application and detection device;
    boosting the analog signals from the force sensors;
    converting the analog signals from the force sensors to digital values;
    calculating load values based on the digital values;
    increasing or decreasing forces on the tested medium to maintain a substantially constant force on the tested medium;
    providing a graphical display of the load values in the form of data points; and
    displaying the limits of permissible deviation of values from an envelope of acceptable force, further including the step of receiving video signals from cameras monitoring the tested medium.

12. The method for monitoring and controlling lateral and vertical forces of claim 11 further including the step of storing the video signals.

* * * * *